(12) United States Patent
Brahm et al.

(10) Patent No.: US 10,010,659 B1
(45) Date of Patent: Jul. 3, 2018

(54) METHOD OF STERILE COLLECTION OF AMNIOTIC FLUID

(71) Applicant: BioDlogics, LLC, Cordova, TN (US)

(72) Inventors: Tim Brahm, Memphis, TN (US); Kevin Foley, Memphis, TN (US)

(73) Assignee: BioDlogics, LLC, Cordova, TN (US)

( * ) Notice: Subject to any disclaimer, the term of this patent is extended or adjusted under 35 U.S.C. 154(b) by 266 days.

(21) Appl. No.: 14/982,949

(22) Filed: Dec. 29, 2015

Related U.S. Application Data

(60) Provisional application No. 62/098,006, filed on Dec. 30, 2014.

(51) Int. Cl.
*A61M 1/00* (2006.01)
*A61M 25/10* (2013.01)
*A61B 5/04* (2006.01)

(52) U.S. Cl.
CPC ........ *A61M 1/0088* (2013.01); *A61M 1/0023* (2013.01); *A61M 25/1011* (2013.01); *A61M 2202/0494* (2013.01)

(58) Field of Classification Search
CPC ............ A61M 1/00; A61M 25/10; A61B 5/04
See application file for complete search history.

(56) References Cited

U.S. PATENT DOCUMENTS

| | | | | |
|---|---|---|---|---|
| 5,527,336 | A * | 6/1996 | Rosenbluth | A61F 2/958 600/116 |
| 6,104,941 | A * | 8/2000 | Huey | A61B 5/0448 600/338 |
| 8,408,212 | B2 * | 4/2013 | O'Brien | A61B 17/0057 128/830 |
| 8,932,805 | B1 * | 1/2015 | Brahm | C12N 5/0605 435/1.3 |
| 9,855,301 | B1 * | 1/2018 | Brahm | A61K 35/51 |
| 2007/0203445 | A1 * | 8/2007 | Kaye | A61M 1/3653 604/6.16 |
| 2016/0135843 | A1 * | 5/2016 | Chinchoy | A61B 5/04 606/124 |

* cited by examiner

*Primary Examiner* — Tatyana Zalukaeva
*Assistant Examiner* — Sara Sass
(74) *Attorney, Agent, or Firm* — Brinks Gilson & Lione

(57) ABSTRACT

A method for sterilely recovering amniotic fluid is provided. The amniotic fluid is used for regenerative medicine purposes. The method utilizes a suction device that does not harm the infant.

11 Claims, 1 Drawing Sheet

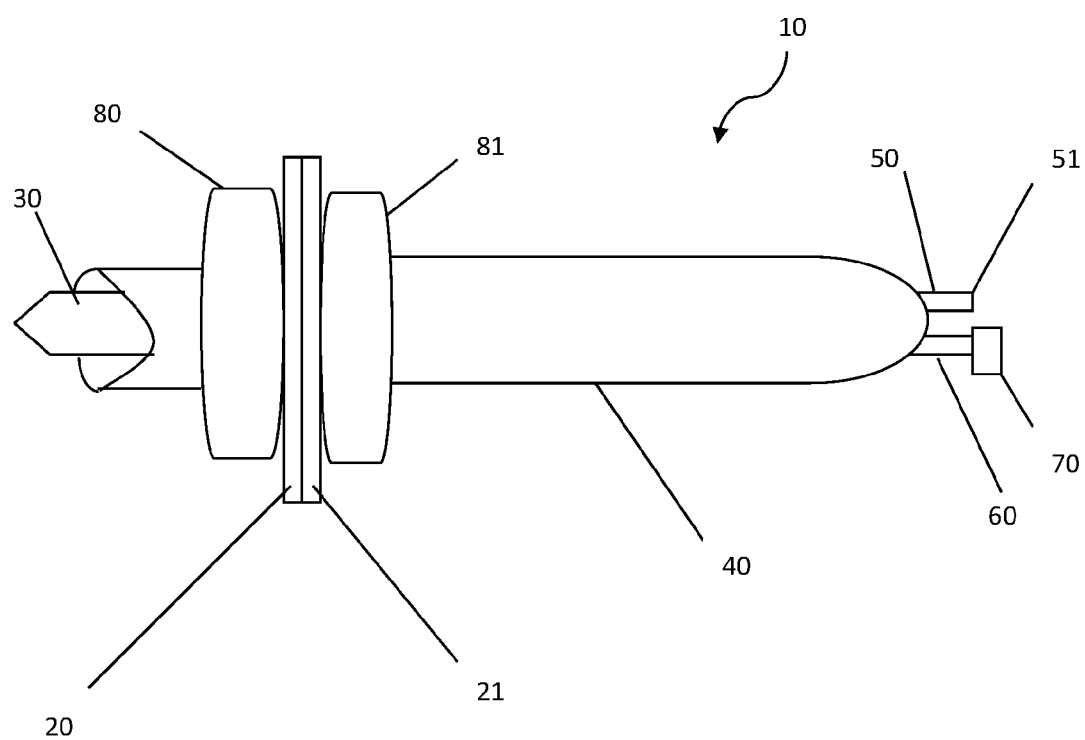

US 10,010,659 B1

METHOD OF STERILE COLLECTION OF AMNIOTIC FLUID

CROSS-REFERENCE TO RELATED APPLICATIONS

The present application claims priority to U.S. Provisional Application No. 62/098,006 filed Dec. 30, 2014.

BACKGROUND OF THE INVENTION

Amniotic fluid is commonly recovered through various techniques known in the art such, for example, amniocentesis. Known techniques typically involve the use of syringes that utilize needles, including blunt needles, which may put the unborn fetus at risk for harm or infection. An issue arising when preparing a regenerative or therapeutic product from amniotic fluid is that of maternal contaminants from the puncture site of the amniotic sac mixing with the amniotic fluid. Maternal blood dispersed within the amniotic fluid of a regenerative or therapeutic product may cause rejection in a future recipient.

Thus, there remains a need for a means of obtaining sterile amniotic fluid that does not present the aforementioned issues.

SUMMARY OF THE INVENTION

According to one aspect, a method of sterile collection of amniotic fluid from an amniotic sac during a Cesarean section procedure is provided. The method includes the steps of forming an incision in the amniotic sac while the amniotic sac is exposed prior to removal of an infant during a Cesarean section procedure, the amniotic sac comprising amnion and chorion; positioning a blunt tip of a suction device through the incision and into the amniotic sac such that the blunt tip is in contact with any amniotic fluid present inside the amniotic sac; positioning a first balloon of the suction device on a proximal side of the amnion relative to an infant in the amniotic sac; positioning a second balloon of the suction device on a distal side of the chorion relative to the infant in the amniotic sac; inflating the first balloon; inflating the second balloon; and applying air flow through the suction device such that amniotic fluid within the amniotic sac flows from the amniotic sac, through the blunt tip of the suction device and into a collection container. The amniotic fluid remains sterile upon entry into the collection container. According to one embodiment, the suction device is in communication with and attached to at least one tube for delivering amniotic fluid from the blunt tip of the suction device to the collection container. According to one embodiment, the suction device, at least one tube and collection container are sterilely treated prior to use. According to one embodiment, the sterilely collected amniotic fluid is preserved and subsequently utilized in regenerative medicine applications. According to one embodiment, the first balloon and second balloon prevent maternal blood and amniotic fluid from mixing. According to one embodiment, the suction device includes a flexible tube, wand, trocar, or catheter. According to one embodiment, the trocar is a blunt cannulated trocar. According to one embodiment, air flow is supplied by at least one pump or syringe. According to one embodiment, the pump is in air communication with the suction device and container such that amniotic fluid is moved through the blunt tip of the suction device and into the collection container. According to one embodiment, the first and balloon are inflated simultaneously. According to one embodiment, imaging equipment is utilized to aid in the proper placement of the blunt tip within the amniotic sac.

According to another aspect, a method of sterile collection of amniotic fluid from an amniotic sac during a Cesarean section procedure is provided. The method includes the steps of forming an incision in the amniotic sac while the amniotic sac is exposed prior to removal of an infant during a Cesarean section procedure, the amniotic sac comprising amnion and chorion; positioning and applying a suction cup of a suction device on a distal side of the chorion relative to the infant in the amniotic sac; inserting a blunt tip of the suction device containing a suction cup through the incision and into the amniotic sac such that the blunt tip is in contact with any amniotic fluid present inside the amniotic sac; and applying air flow through the suction device such that amniotic fluid within the amniotic sac flows from the amniotic sac, through the blunt tip of the suction device and into a collection container. The amniotic fluid remains sterile upon entry into the collection container. According to one embodiment, the suction device is in communication with and attached to at least one tube for delivering amniotic fluid from the blunt tip of the suction device to the collection container. According to one embodiment, the suction device, suction cup, at least one tube and collection container are sterilely treated prior to use. According to one embodiment, the sterilely collected amniotic fluid is preserved and subsequently utilized in regenerative medicine applications. According to one embodiment, the suction device includes a flexible tube, wand, trocar, or catheter. According to one embodiment, the trocar is a blunt cannulated trocar. According to one embodiment, the air flow is supplied by at least one pump or syringe. According to one embodiment, the pump is in air communication with the suction device and container such that amniotic fluid is moved through the blunt tip of the suction device and into the collection container. According to one embodiment, imaging equipment is utilized to aid in the proper placement of the blunt tip within the amniotic sac.

BRIEF DESCRIPTION OF THE DRAWINGS

FIG. 1 illustrates a suction device for the sterile removal of amniotic fluid according to one embodiment.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements.

As used in the specification, and in the appended claims, the singular forms "a", "an", "the", include plural referents unless the context clearly dictates otherwise.

The term "amniotic sac" as used herein refers to the bag in which the fetus develops that retains amniotic fluid and includes an inner amnion and outer chorion membrane layer.

The terms "sterile" and "aseptic" may be used interchangeably and refer to the absence of all live microorganisms, including pathogenic microorganisms such as, for example, bacteria.

A method of sterile collection of amniotic fluid is provided. The method is conducted in a manner that prevents the mixing of amniotic fluid and maternal blood. The method is conducted during a Cesarean section procedure prior to removal of the infant from the amniotic sac. The amniotic fluid collected from the method may be utilized exclusively for use in regenerative medicine applications and is not utilized for diagnostic use.

According to one embodiment, the method includes the step of cutting, piercing, puncturing or forming an incision site in the amniotic sac while the amniotic sac is exposed during a Cesarean section procedure. The method further includes the step of positioning a suction device with a blunt tip through the incision site and into the amniotic sac. The blunt tip is placed in contact with amniotic fluid located within the amniotic sac. A first and second balloon may be located on or within the suction device (see Example; see FIG. 1). Upon positioning the suction device through the incision site, the first balloon is positioned on a proximal side of the amnion relative to the infant. The second balloon is, in turn, positioned on a distal side of the chorion relative to the infant. Prior to or at approximately the same time as collection of the amniotic fluid, each balloon is inflated. Air flow or pressure (e.g., negative air flow or pressure) is applied through the suction device causing amniotic fluid in contact with the blunt tip of the suction device to move through the blunt tip and into a collection container attached to the device. The collected amniotic fluid is then preserved according to acceptable preservation procedures known the art (e.g., cryopreservation) until use in a regenerative medicinal application.

According to one embodiment, a gas (e.g., air) is moved through the device by any suitable source or means of applying negative flow or pressure. By moving air through the device, suction is created thereby assisting in the movement of amniotic fluid through the device. Suitable sources of air flow or pressure include a pump or a syringe that is in communication with the collection container and the suction device. According to one embodiment, the pump is located external to the collection container such that air is moved through the container and out of the pump. Alternatively, the pump may be located within the collection container and the collection container may include a vent to allow gas to flow out of the container. A regulator may be arranged between the gas flow source and the storage container. The regulator may include a flowmeter with flowrate reading and regulating functions. The regulator may include a regulation knob for user control of the amount and velocity of gas flow or pressure applied to the suction device.

According to one embodiment, tubing connects the suction device to the collection container and provides a means of communication between the device and collection container. The tubing may also connect to at least one pump or syringe. The tubing may also be connected to or include a blunt tip as provided herein. The tubing is preferably made of a flexible material, which is sterile or capable of being sterilized. The tubing assists in the movement of amniotic fluid through the suction device and into the collection container. Suitable materials include, but are not limited to, silicone elastomer, ethyl, vinyl acetate, latex, polyethylene, polypropylene, or vinyl (flexible PVC).

According to one embodiment, the collection container is fabricated from any material suitable for sterile collection and storage of amniotic fluid. The collection container may be a size such that the internal capacity substantially matches the average amount of amniotic fluid collected from the amniotic sac. Thus, the container may be sized such that excess space after collection is minimized thereby facilitating portability and storage. The overall container shape may be of any shape such the container is easily moved and portable from the site of collection to storage. The container may optionally include one or more handles and a removable top. The container may further include an inlet for engaging at least one tube which delivers incoming amniotic fluid.

According to one embodiment, the suction device includes a flexible tube, wand, catheter, cannulated trocar, or any other suitable device that includes a blunt tip and will not inflict injury to the infant. The suction device does not include any needle, including needles with a blunt tip, or any other device capable of piercing or harming the infant. According to one embodiment, the method is carried out using a suction device that includes a blunt, cannulated trocar. According to one embodiment, the trocar is adapted for insertion into the amniotic sac.

According to a particular embodiment, the suction device may optionally include a trocar equipped with a suction cup at its tip. The suction cup may be positioned and applied to the distal side of the chorionic membrane to steady or stabilize the device immediately prior to insertion of the blunt, cannulated trocar head into the membranes (amnion and chorion). Application of the suction cup prevents the device from slipping out of the amniotic sac, in addition to aiding in sealing the perforations caused by the entry of the device into the amnion and chorion membranes to prevent amniotic fluid loss. Furthermore, application of the suction cup prevents further tearing or rupturing of the membranes and prohibits maternal blood from entering into the amniotic sac (i.e., prohibits cross-contamination of maternal blood and amniotic fluid). The amniotic fluid may then be suctioned or removed through any tubing attached thereto and delivered into a collection container.

According to a particular embodiment, the suction device includes a first balloon that is positioned on the proximal side of the amnion relative to the infant and a second balloon that is positioned on the distal side of the chorion relative to the infant during use (see e.g., Example, infra). The first and second balloons may be inflated once positioned thereby sealing the incision or any perforation(s) caused by the entry of the suction device into the amniotic and chorionic membranes to prevent amniotic fluid loss and tearing or rupturing of the amniotic and chorionic membranes. The first and second balloons may be connected to or otherwise in gas communication with any gas source suitable for inflation of a balloon for medical applications. Suitable gases include ambient, surrounding air, nitrogen, or any other acceptable gas for internal balloon use. According to an alternative embodiment, the first and second balloons can be inflated with at least one sterile fluid (e.g., water) after proper positioning of the device. According to one embodiment, each of the first and second balloons is inflated to an appropriate diameter to seal any opening and prevent amniotic fluid loss and/or tearing or rupturing of the amniotic and chorionic membranes. According to one embodiment, each of the first and second balloons is independently connected to a gas or liquid source via at least one tube, lumen, or a combination thereof. Inflation may be assisted or otherwise regulated by at least one valve in communication with the at least one tube, lumen, or a combination thereof. Each of the first and second balloons may be inflated sequentially or simultaneously.

According to one embodiment, amniotic fluid may be collected or otherwise removed or drained from the amniotic sac through the suction device and into a collection container after the first and second balloons are inflated. After suction is complete, each of the first and second balloons is deflated. The suction device may then be removed from the incision. The surgeon or other medical profession may then proceed with the appropriate steps of a Caesarean section procedure.

According to one embodiment, the suction device, tubing, and collection container are treated according to any acceptable method known in the art to remove any pathogens prior to use to ensure sterile collection of the amniotic fluid.

According to one embodiment, the methods as provided herein may include the use of imaging equipment to aid in the proper placement of the suction device. Suitable imaging equipment includes, but is not limited to, sonogram or ultrasound.

Also provided herein is a kit including at least one suction device, suction cup, pump, syringe, collection container and any associated tubing or lumen. The kit is appropriately sterilized and preserved up until and during shipment to a distributor or medical facility. The kit additionally includes at least one set of instructions for the end user (i.e., medical professional).

EXAMPLE

Obtaining amniotic fluid from a mother can be achieved utilizing the embodiment of a suction device as illustrated in FIG. 1. As illustrated in FIG. 1, the suction device 10 includes a first balloon 80 and second balloon 81 which seals the proximal side of the amnion 20 and the distal side of the chorion 21, respectively. According to the illustrated embodiment, a flexible tube 40 encompasses a first lumen 50 and a second lumen 60. The first lumen 50 includes a cannulated trocar 30 capable of passing through the amnion 20 and chorion 21. The first lumen 50 is open at a proximal end 51 and distal end (not shown), allowing amniotic fluid to drain into a sterile collection container (not shown). The second lumen 60 has a valve 70 and is in gas communication with or otherwise connects to the first and second balloon (80, 81).

To use the device of FIG. 1, the user (e.g., medical professional) initially makes a small perforation or incision in the amniotic sac prior to removal of the child during a Caesarean section procedure. The user inserts the blunt, cannulated trocar 30 into and through the incision site (i.e., through the amnion 20 and chorion 21). A first balloon 80 can be positioned on the proximal side of the amnion relative to the infant. A second balloon 81 can be positioned on the distal side of the chorion relative to the infant. At a certain point either prior to or during withdrawal of amniotic fluid through the first lumen 50, the first and second balloons (80, 81) can be triggered to inflate via the valve 70 on the second lumen 60. The device 10 can use gravity, womb pressure, positive gas flow, or negative vacuum suction to inflate the balloons (80, 81) after proper positioning of the device 10. The balloons (80, 81) can be alternatively inflated with sterile water after proper positioning of the device 10. Inflation of the balloons (80, 81) prevents the device 10 from slipping out of the amniotic sac, in addition to sealing the perforations caused by the entry of the device 10 into the amnion 80 and chorion 81 to prevent amniotic fluid loss. Furthermore, inflation of the balloons (80, 81) prevents further tearing or rupturing of the membranes and prohibits maternal blood from entering into in the amniotic sac (i.e., prohibits cross-contamination of maternal blood and amniotic fluid). The amniotic fluid may then be suctioned or removed through the first lumen 50, through any tubing attached thereto (not shown), and delivered into a collection container (not shown).

The entire suction device 10 and associated tubing can be manufactured from any appropriate materials capable of sterilization, such as silicone rubber, natural rubber, or plastic. The balloons (80, 81) may be fabricated from PVC, polyurethane, a silicon-based material, or a combination thereof.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:

1. A method of sterile collection of amniotic fluid from an amniotic sac during a Cesarean section procedure, the method comprising the steps of:
   forming an incision in the amniotic sac while the amniotic sac is exposed prior to removal of an infant during a Cesarean section procedure, the amniotic sac comprising amnion and chorion;
   positioning a blunt tip of a suction device through the incision and into the amniotic sac such that the blunt tip is in contact with any amniotic fluid present inside the amniotic sac;
   positioning a first balloon of the suction device on a proximal side of the amnion relative to an infant in the amniotic sac;
   positioning a second balloon of the suction device on a distal side of the chorion relative to the infant in the amniotic sac;
   inflating the first balloon;
   inflating the second balloon; and
   applying air flow through the suction device such that amniotic fluid within the amniotic sac flows from the amniotic sac, through the blunt tip of the suction device and into a collection container,
   wherein the amniotic fluid remains sterile upon entry into the collection container.

2. The method of claim 1, wherein the suction device is in communication with and attached to at least one tube for delivering amniotic fluid from the blunt tip of the suction device to the collection container.

3. The method of claim 2, wherein the suction device, at least one tube and collection container are sterilely treated prior to use.

4. The method of claim 1, wherein the sterilely collected amniotic fluid is preserved and subsequently utilized in regenerative medicine applications.

5. The method of claim 1, wherein the first balloon and second balloon prevent maternal blood and amniotic fluid from mixing.

6. The method of claim 1, wherein the suction device includes a flexible tube, wand, trocar, or catheter.

7. The method of claim 6, wherein the trocar is a blunt cannulated trocar.

8. The method of claim 1, wherein the air flow is supplied by at least one pump or syringe.

9. The method of claim 8, wherein the pump is in air communication with the suction device and container such that amniotic fluid is moved through the blunt tip of the suction device and into the collection container.

10. The method of claim 1, wherein the first and balloon are inflated simultaneously.

11. The method of claim 1, wherein imaging equipment is utilized to aid in the proper placement of the blunt tip within the amniotic sac.

\* \* \* \* \*